Figure 1:
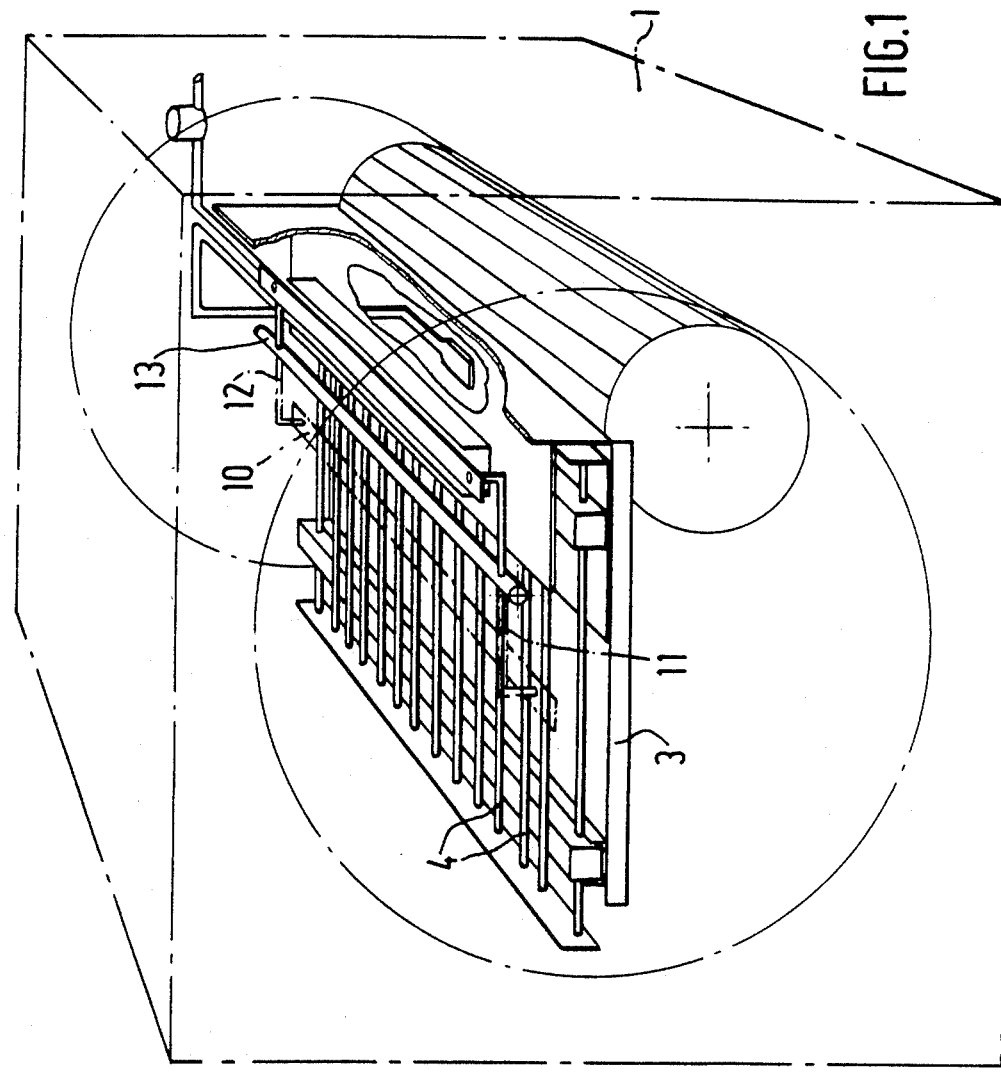

United States Patent [19]

Angelier et al.

[11] Patent Number: 4,580,409
[45] Date of Patent: Apr. 8, 1986

[54] DEVICE FOR FREEZING BIOLOGICAL PRODUCTS CONTAINED IN STRAWS

[75] Inventors: Nicole Angelier, Echirolles; Francois Colomb, Grenoble, both of France

[73] Assignee: L'Air Liquide, Societe Anonyme pour l'Etude et l'Exploitation des Procedes Georges Claude, Paris, France

[21] Appl. No.: 688,765

[22] Filed: Jan. 4, 1985

[30] Foreign Application Priority Data

Jan. 19, 1984 [FR] France ............................ 84 00791

[51] Int. Cl.⁴ .................................................. F25C 1/00
[52] U.S. Cl. .......................................... 62/340; 62/60; 62/78; 62/383; 62/514 R; 426/85
[58] Field of Search ................. 62/4, 60, 78, 383, 457, 62/529, 530, 531, 514 R, 340; 426/85, 524

[56] References Cited

U.S. PATENT DOCUMENTS 2,591,375 4/1952 Radford ................................ 62/530
2,746,265 5/1956 Mills .......................................... 62/4
4,091,632 5/1978 Marchewka et al. ..................... 62/1
4,134,494 1/1979 Wong ..................................... 426/85

FOREIGN PATENT DOCUMENTS 2455718 11/1980 France .

*Primary Examiner*—Ronald C. Capossela
*Attorney, Agent, or Firm*—Young & Thompson

[57] ABSTRACT

The invention relates to the freezing of biological products contained in straws and more particularly to the initiation of the crystallization phase. A series of straws is disposed in such manner that the straws are arranged in parallel side-by-side relation and a crystallization bar (10) is mounted by springs (20) on two arms (11 and 12) connected to a rotary shaft (13). The arms shift the bar between a waiting position in a receiver-cradle (16) which is deeply cooled by a pipe (17–18) and an operative position in which is bears against the straws. Application in the freezing of blood cells, human and animal sperm, fragments of biological tissues and embryos, etc.

8 Claims, 5 Drawing Figures

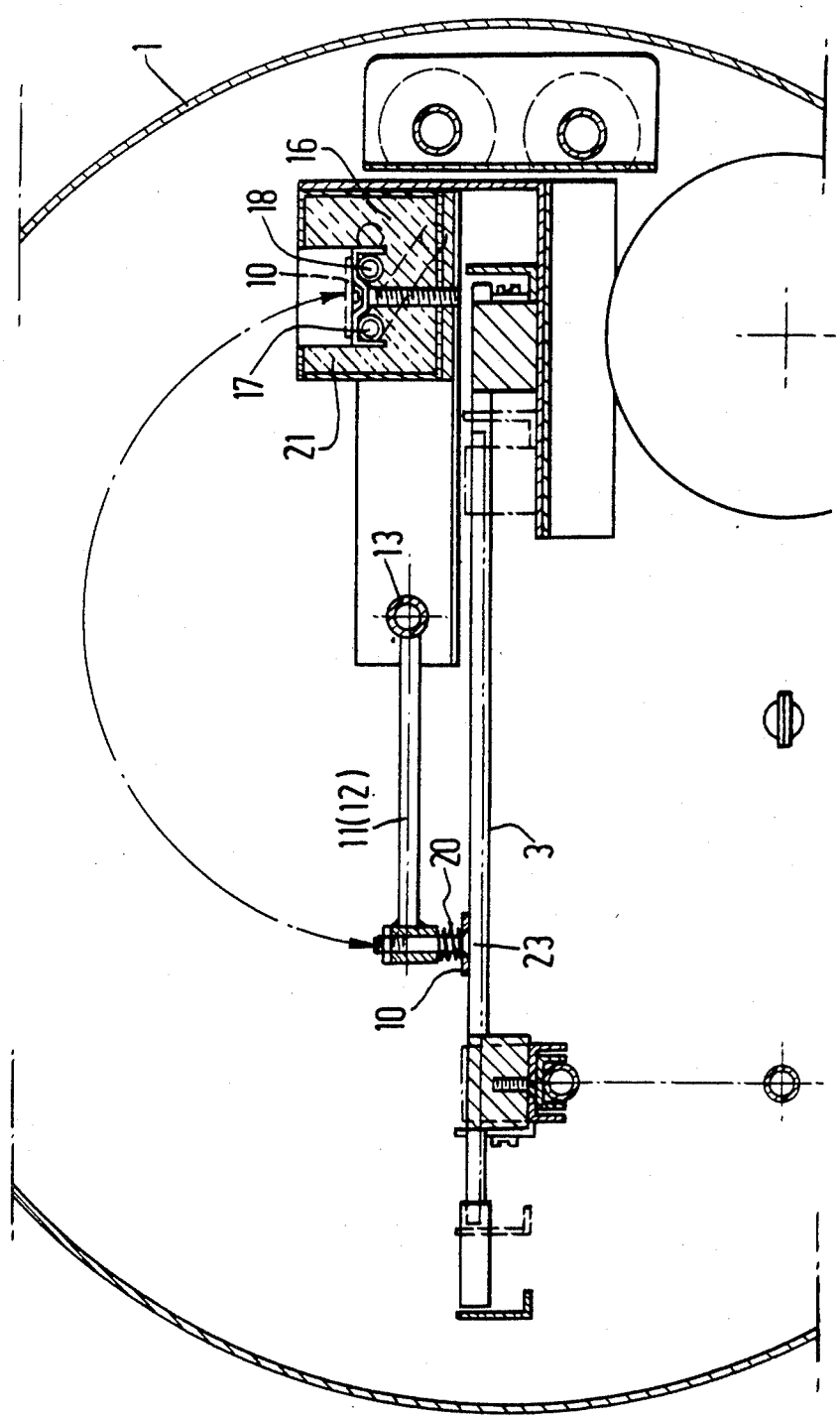

DEVICE FOR FREEZING BIOLOGICAL PRODUCTS CONTAINED IN STRAWS

The invention relates to a device for freezing biological products contained in straws.

It is known that, for the purpose of storing some biological products in the frozen state, it is essential to proceed to a programmed cooling of the product so that it reaches the solid state, this cooling and the storage being effected in containers cooled with liquid nitrogen. The passage from the liquid state to the solid state, or crystallization, is always preceded by a surfusion which may be prolonged at relatively low temperatures distinctly lower than the theoretical temperature of freezing, depending on the state of the biological product and the presence or absence of a crystalline seed. Thus it cannot be determined in a precise manner with existing programmable freezers and it has been proposed to ensure the initiation of this crystallization by a mechanical or thermal shock which induces crystallization, this being effected at a precise cold temperature which ensures the best survival of the biological products. Generally, a thermal shock is produced in the straws by a manual contact for a short period of time of a cold finger initiating crystallization. This operation is carried out manually and results in loss of time and certain difficulties since, for example in the case of embryos, the embryo itself must not be directly acted upon. Further, the freezing container must be open and this disturbs the whole cooling cycle.

An object of the present invention is to automatically produce a mechanical or thermal shock inducing crystallization at a given temperature so as to avoid an excessive surfusion.

Another object of the invention, which is more particularly applicable to the freezing of embryos which are immersed in a cryoprotective solution in a longitudinally determined region of a straw, is to carry out a thermal shock inducing crystallization in such a longitudinally determined region for each straw.

The freezing device according to the invention includes an inductor of elongated shape associated with means for displacing it from a deep cooling receiving cradle to a transverse position in which it bears on said straws.

Figure 2:
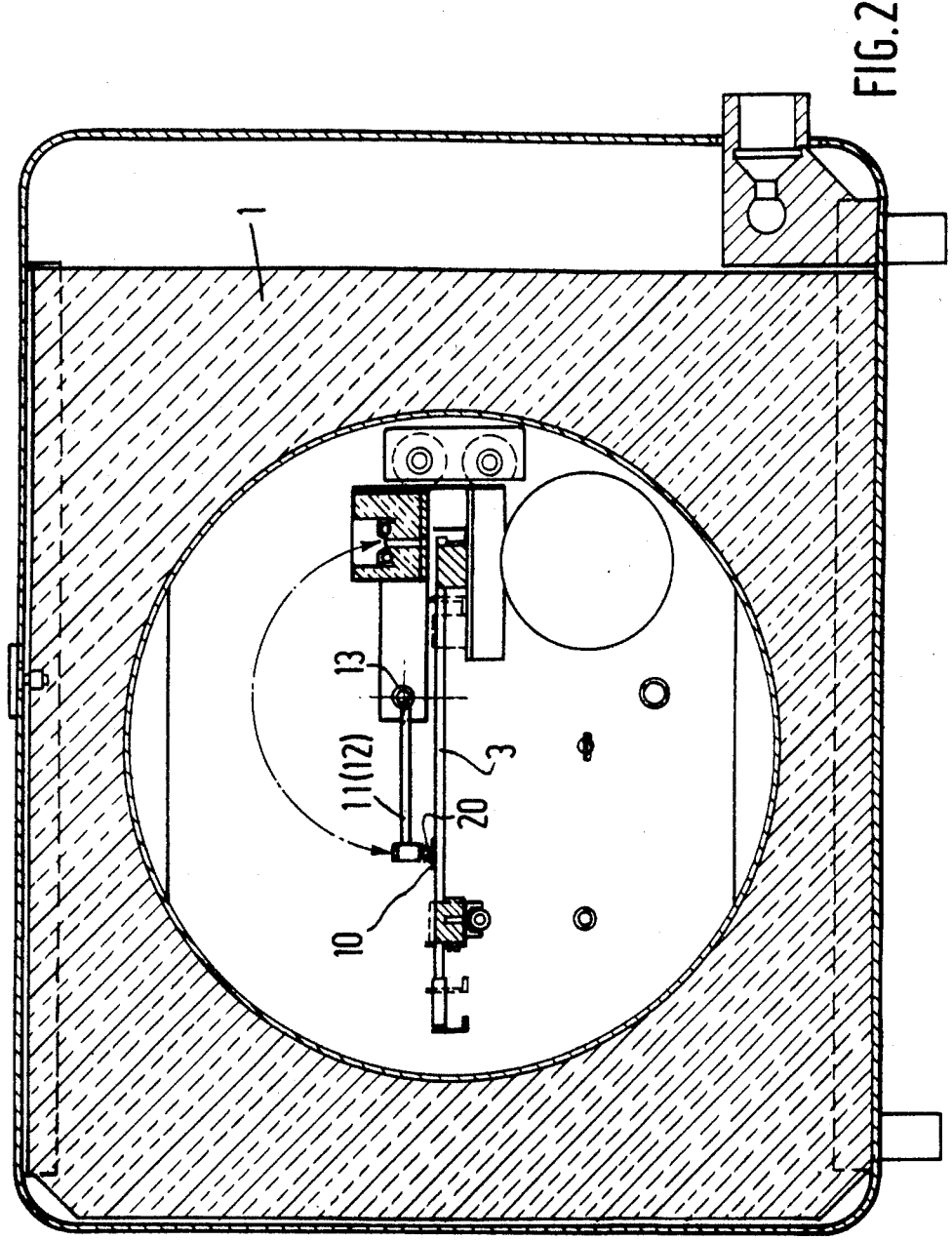
Figure 3:
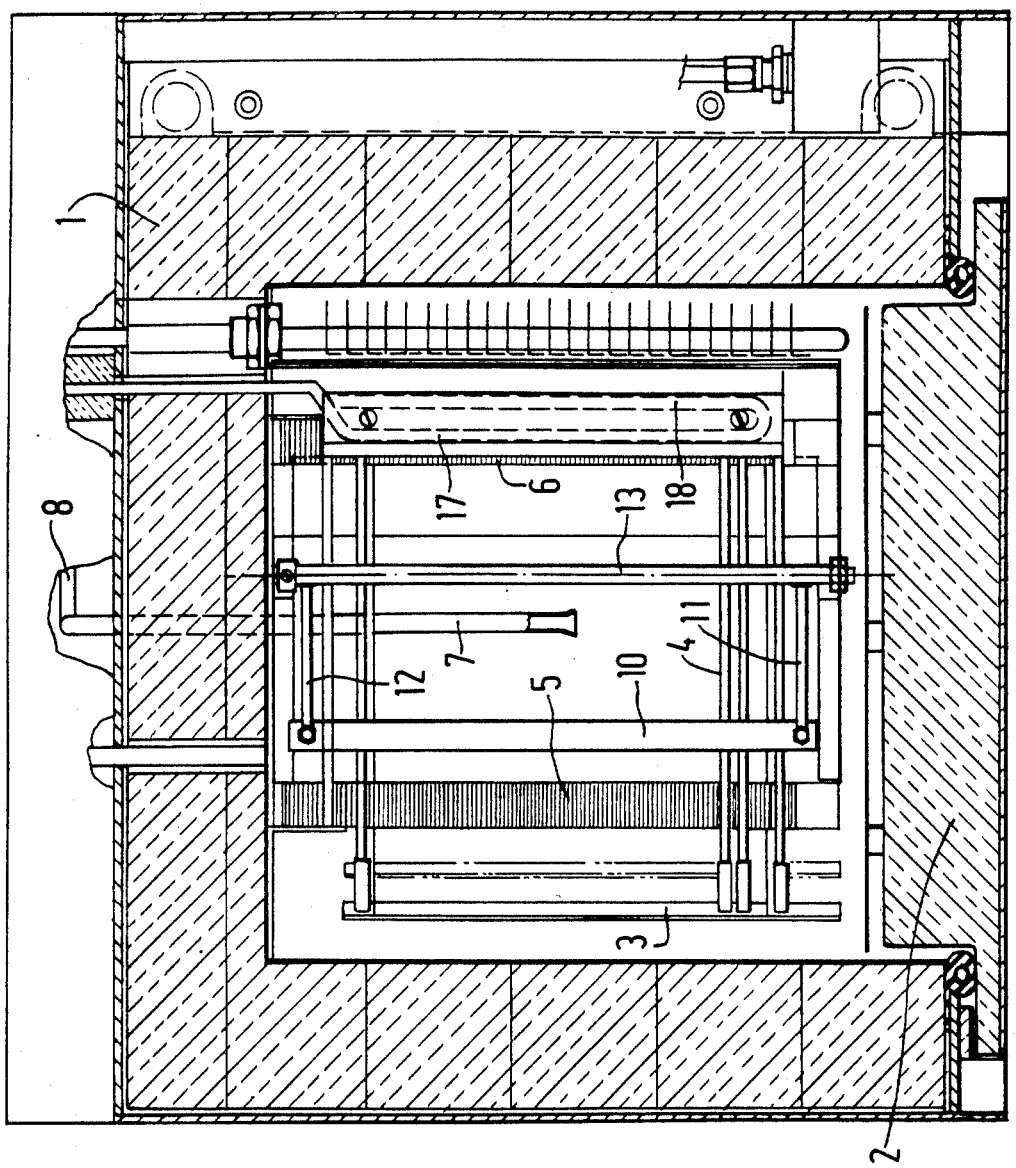
Figure 4:
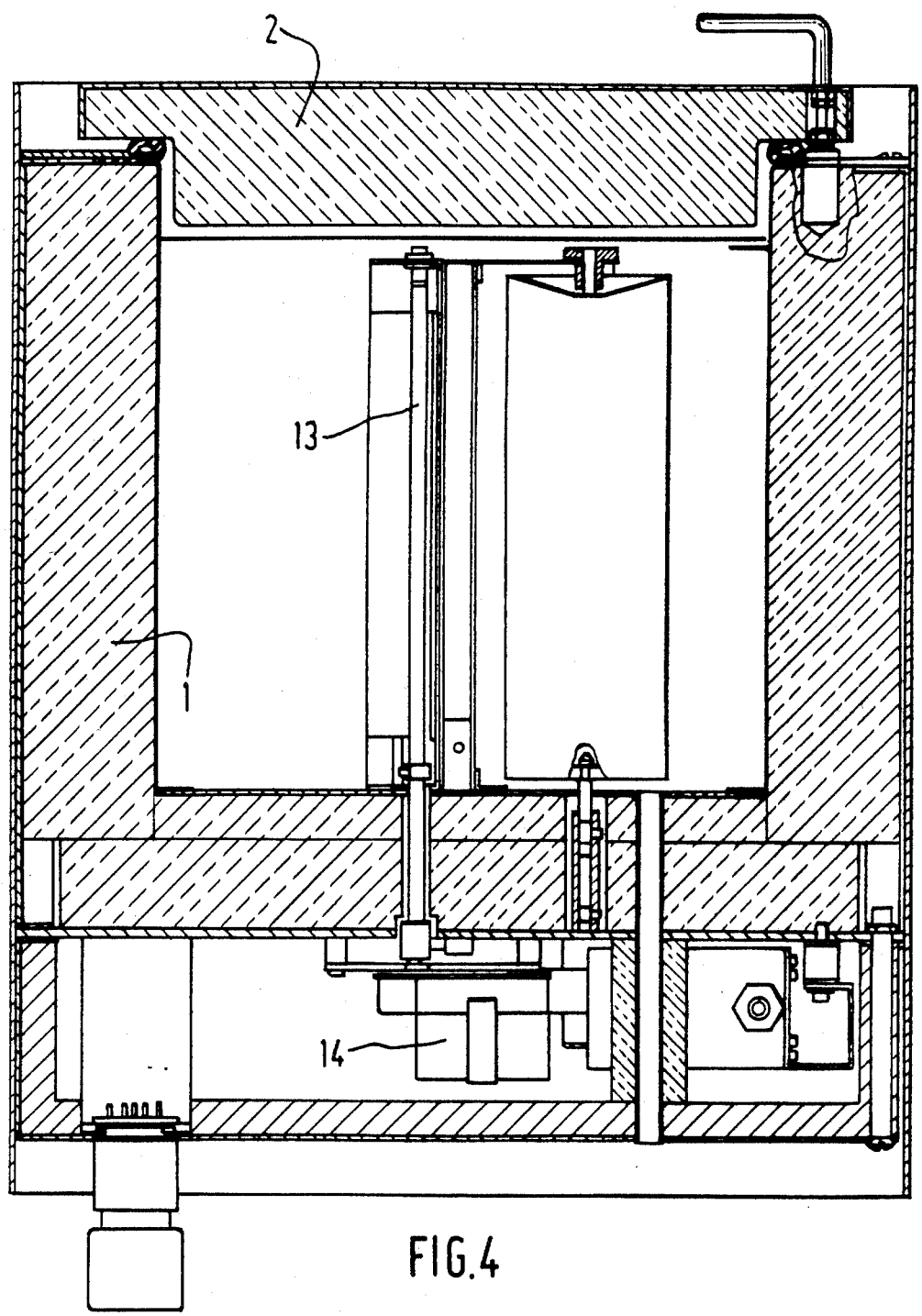

The invention will now be described with reference to the accompanying drawings in which:

FIG. 1 is a perspective view of the device;
FIG. 2 is a vertical sectional view;
FIG. 3 is a horizontal sectional view;
FIG. 4 is another horizontal sectional view, and
FIG. 5 is an enlarged view of a part of FIG. 2.

With reference to the accompanying drawings, a freezing device according to the invention comprises a thermal insulation container 1 provided with an entry door 2, in which is mounted a support carriage 3 for biological straws 4 arranged to be parallel to each other by engagement in two transverse racks 5 and 6 of the support carriage 3. The container also includes a liquid nitrogen injector 7 supplied with liquid nitrogen through a pipe 8 having a valve. Mounted inside the container is a crystallization inductor formed by a metal bar 10 transversely extending relative to the support carriage 3 and connected by springs 20 to two shifting arms 11 and 12 which are mounted on a shaft 13 which extends through the container wall and can be driven in rotation by a motor 14. At one end of the rotary movement of the shaft 13 through 180°, the crystallization inducing bar 10 bears on top of the set of straws 4 (see FIGS. 2 and 5) so as to produce in certain given regions of the straws a thermal shock initiating the crystallization. At the other end of the movement, the crystallization inducing bar 10 bears against a receiver-cradle 16 with an insulated wall 21 on the bottom of which is disposed a looped conduit 17 and 18 supplied in series with the pipe 8 downstream of the supply-stop valve 9. Thus it will be understood that, in the waiting position, in which the crystallization bar 10 is supported in the receiver-cradle 16, it is cooled substantially to the temperature of the liquid nitrogen and that, during the brief period of time during which it bears against the straws 4, which are at the temperature prevailing inside the container, on the order of a few degrees below 0°, this bar 10 provides a thermal shock on the product inside each straw 4 and thus brings about a commencement of the crystallization. This bearing of the bar 10 against the straws 4 usually lasts between a few tenths of a second to a few seconds.

In some cases, when it concerns a biological product distributed along the entire length of the straws, the longitudinal region in which the thermal shock is produced is of little importance but, in other cases, in particular when it concerns embryos which are disposed in a cryoprotective liquid segment in a precise longitudinal region of each straw, while the remaining parts of the straws on each side of this cryoprotective liquid segment are filled with another liquid which is separated from the cryoprotective liquid by two bubbles of air, the thermal shock must occur precisely in the region of the cryoprotective liquid and above the straws so as to avoid affecting the embryo which rests at the bottom of the straw. This double condition makes it necessary in this type of application, to arrange that the crystallization inducing bar comes into contact with the top of all the straws and not below, and to arrange all the straws longitudinally in position on the support carriage 3 so that the cryoprotective liquid segment is on the impact path of the bar. For this purpose, the support carriage 3 is mounted to be longitudinally adjustable by means of a rod 23 which cooperates with an adjusting screw. Further, the temperature inside the container must be very precisely watched and controlled and, for this purpose, there has been disposed in a bottom straw a thermometric probe which consists of a flexible wire connected to the programmer located outside. In this way, it can be made sure that the temperature measured in this straw, which incorporates solely cryoprotective liquid, is representative of the temperature of the biological products in all the other straws.

The invention concerns biological products contained in straws for the purpose of being frozen and stored with liquid nitrogen, and more particularly blood cells, human and animal sperm, fragments of biological tissues, and embryos of different animal origins, etc.

What is claimed is:

1. A device for freezing biological products contained in straws, said device comprising a thermally insulated container having an entrance door, a support carriage located within said container for supporting the biological straws, said carriage being adapted to receive said straws in such manner that said straws are parallel to one another, controlled cooling means located within said container comprising a liquid nitrogen injector and means for stirring a gaseous atmosphere within said container, said device further comprising a crystallization inducing means, located within said chamber, comprising an elongated member movable between a first and a second position, a receiver-cradle for receiving and deeply cooling said crystallization inducing means in said first position, and means associated with said crystallization inducing means for shifting said crystallization inducing means between said first position in said receiver-cradle and said second position wherein said crystallization inducing means bears against said straws and is oriented transversely in relation to the straws.

2. A device for freezing biological products contained in straws according to claim 1, wherein said crystallization inducing means is a metal bar and said shifting means comprise shifting arms carrying said metal bar.

3. A device for freezing biological products contained in straws according to claim 2, wherein said shifting means comprise a shaft on which said shifting arms are mounted, said shaft extending through a wall of said container, and a motor drivingly connected to said shaft.

4. A device for freezing biological products contained in straws according to claim 1, wherein said shifting means are arranged in such manner that said crystallization inducing means approaches the support of the straws in a downward direction in assuming its said second position.

5. A device for freezing biological products contained in straws according to claim 1, wherein said receiver-cradle comprises an exchanger tube and a liquid nitrogen supply conduit such that said nitrogen injector and said exchanger tube are connected in series with said conduit, said conduit comprising a supply-stop valve in common with said exchanger tube and said nitrogen injector.

6. A device for freezing biological products contained in straws according to claim 1, wherein said controlled cooling means comprises heating means for providing a fine control of said cooling.

7. A device for freezing biological products contained in straws according to claim 1, and a thermal probe in the form of a flexible wire for engagement in a straw.

8. A device for freezing biological products contained in straws according to claim 1, wherein the support carriage for the straws is so arranged that the straws are horizontal.

* * * * *